(12) United States Patent
Park

(10) Patent No.: US 8,187,650 B2
(45) Date of Patent: May 29, 2012

(54) EGG TRAY AND FIXER AND METHOD OF PROCESSING EGGS USING THE SAME

(76) Inventor: Joong-Min Park, Goyang (KR)

(*) Notice: Subject to any disclaimer, the term of this patent is extended or adjusted under 35 U.S.C. 154(b) by 491 days.

(21) Appl. No.: 12/190,704

(22) Filed: Aug. 13, 2008

(65) Prior Publication Data

US 2010/0040744 A1 Feb. 18, 2010

(51) Int. Cl.
*A21D 6/00* (2006.01)
(52) U.S. Cl. ........ 426/248; 426/302; 426/614; 426/407; 426/509; 426/523; 426/298; 426/301; 426/521; 426/308
(58) Field of Classification Search .................. 426/298, 426/302, 614, 407, 521, 248, 301, 523, 308
See application file for complete search history.

(56) References Cited

U.S. PATENT DOCUMENTS

| 3,830,945 A | * | 8/1974 | Scharman | 426/243 |
| 4,355,731 A | * | 10/1982 | Carroll et al. | 217/26.5 |
| 5,340,596 A | * | 8/1994 | Ohgake et al. | 426/301 |
| 5,694,836 A | * | 12/1997 | Blevins | 99/517 |
| 5,939,119 A | * | 8/1999 | Cheng et al. | 426/302 |
| 2002/0006456 A1 | * | 1/2002 | Yamazaki | 426/241 |
| 2007/0148316 A1 | * | 6/2007 | Lee | 426/614 |

FOREIGN PATENT DOCUMENTS

KR 20080054653 * 6/2008

OTHER PUBLICATIONS

Translation of KR20080054653.*

* cited by examiner

Primary Examiner — Drew Becker
Assistant Examiner — Preston Smith
(74) Attorney, Agent, or Firm — Lexyoume IP Group, PLLC.

(57) ABSTRACT

The present invention relates to an egg tray that is used to sterilize an egg or to boil the egg soft or hard and in which an egg is washed, heated, sterilized, boiled soft or hard, dried, coated, inspected, cooled, and packed to increase the safety and the value of commodity of foods and to increase the productivity, a fixer for layering the egg trays to fix them, and a method for processing an egg by using the same. The egg trays of the present invention includes a plurality of convex parts that are disposed at a predetermined interval to be connected to each other, a plurality of bottom parts that are protruded in an opposite direction with respect to the convex parts, and a guide part that is protruded from the center part of the convex part, and in which a plurality of fluid discharging holes that are formed around the guide parts, inclined sides that form lateral parts of the convex parts are convex, a plurality of egg insertion holes are formed on the inclined sides by using the egg trays, and a plurality of fluid discharging holes may be further provided around the bottom part.

9 Claims, 9 Drawing Sheets

EGG TRAY AND FIXER AND METHOD OF PROCESSING EGGS USING THE SAME

BACKGROUND OF THE INVENTION (a) Field of the Invention

The present invention relates to an egg tray that is used to sterilize an egg or to boil the egg soft or hard, an egg tray fixer, and a method for processing the egg by using them. More particularly, the present invention relates to an egg tray in which an egg is washed, heated, sterilized, boiled soft or hard, dried, coated, inspected, and cooled to increase safety and the value of a food commodity and to increase productivity, and a method for processing an egg by using the same.

(b) Description of the Related Art

An egg is sold after it is sterilized or processed in order to cope with various and subdivided requirements of consumers that desire safe eggs that have no risk of salmonella or bird flu, in order to bring about an increase in value thereof. In the processing treatment, eggs are moved to a discrimination device and discriminated, and then they are put in egg trays and subjected to a heating process to be boiled soft or hard, thereby producing products having additional value. Problems occur when eggs are sterilized and boiled soft or hard in that, in a heating processing treatment in a gas (including steam) or liquid, it is necessary to increase the efficiency of the operation of the process and to improve the value of the commodity and the stability thereof, but this has not occurred. If the washing process of the egg is described as an example, the eggs that are put in the egg trays are washed with water or steam. At this time, the freshness is maintained, the safety is improved, and the value of the commodity is maintained by rapidly drying the liquid or the steam that includes water and the coating agent on the eggshell of the egg. However, the liquid or the steam remains in the egg tray in which the eggs are disposed or in the contact area between the egg tray and the eggs for a predetermined time. The remaining fluid damages the cuticles of the eggshell for protecting against infection by external toxic microorganisms, delays the coating process for protecting the eggs by compensating the damaged cuticles, or causes imperfect coating to increase the risk of infection by the toxic microorganisms. In addition, when they are subjected to the processing treatment by using a conventional egg tray, since it is difficult to discriminate eggs that are difficult to be commercialized such as eggs having a cracked shell, eggs in which an impurity is included at the inside or outside thereof, and rotten eggs, there are problems in that bad products are produced and the safety of foods can be reduced.

The above information disclosed in this Background section is only for enhancement of understanding of the background of the invention and therefore it may contain information that does not form the prior art that is already known in this country to a person of ordinary skill in the art.

SUMMARY OF THE INVENTION

Therefore, the present invention has been made keeping in mind the above problems, and an exemplary embodiment of the present invention provides an egg tray for improving the value of the commodity and safety through the processing of the egg and for improving the productivity by reducing the operation time of the process such as the quick drying, and a method for processing an egg by using the same.

The present invention provides egg trays of the present invention including a plurality of convex parts that are disposed at a predetermined interval to be connected to each other, a plurality of bottom parts that are protruded in an opposite direction with respect to the convex parts, and a guide part that is protruded from the center part of the convex part, and in which a plurality of fluid discharging holes are formed around the guide parts, inclined sides that form lateral parts of the convex parts are convex, a plurality of egg insertion holes are formed on the inclined sides by using the egg tray, and a plurality of fluid discharging holes may be further provided around the bottom part.

It is preferable that a plurality of fluid discharging holes that are disposed around the guide part are provided to the convex part.

It is preferable that the egg tray is made of a synthetic resin material and a material that has heat resistance.

It is preferable that the egg tray is made of a transparent material.

It is preferable that there are four egg insertion holes.

An exemplary embodiment of the present invention provides a process for processing eggs by using an egg tray that includes disposing the eggs so that an air chamber of the eggs in the egg tray faces downward, layering a plurality of the egg trays after the eggs are disposed, washing the eggs that are received in the layered egg trays, heating the eggs after the eggs are washed, sterilizing the eggs by heating the eggs, boiling the eggs soft or hard by heating the eggs, drying the eggs after the eggs are sterilized and boiled soft and hard, and coating the eggs by using a mineral oil after the eggs are dried.

It is preferable that the process further includes cooling the eggs after the eggs are coated.

It is preferable that the process further includes irradiating light to the eggs to inspect whether the defects of the eggs are present or not in the processing of the eggs.

It is preferable that the processing of the eggs is carried out by layering a plurality of egg trays and fixing the layered egg trays by using the fixing member.

The present invention provides an egg tray that includes a plurality of convex parts that are disposed at a predetermined interval, a plurality of bottom parts that are protruded in an opposite direction with respect to the convex parts, and a guide part that is protruded from the center part of the convex part, and an egg tray fixer that includes a fixing member that fixes the egg trays to each other by layering a plurality of egg trays.

The fixing member may include a first member that is disposed on the lower part and the lateral part of the layered egg tray, and a second member that is combined with the first member and is disposed on the upper part of the layered egg tray.

The fixing member may include support parts that are disposed on the lateral parts of the layered egg trays, and elastic parts that are extended from a front end of the support part and bent and that elastically support the upper part and the lower part of the layered egg tray.

In the egg tray, the inclined sides that form the lateral part of the convex part are convex, a plurality of egg insertion holes are formed on the inclined side, a plurality of fluid discharging holes are formed in the convex part, and a plurality of other fluid discharging holes may be formed around the bottom part.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION OF THE EMBODIMENTS

These and other objects of the invention will be more fully understood from the following description of the invention, the referenced drawings attached hereto and the claims appended hereto.

Hereinafter, with reference to the accompanying drawings, preferable embodiments of the present invention will be described in detail.

Figure 1:
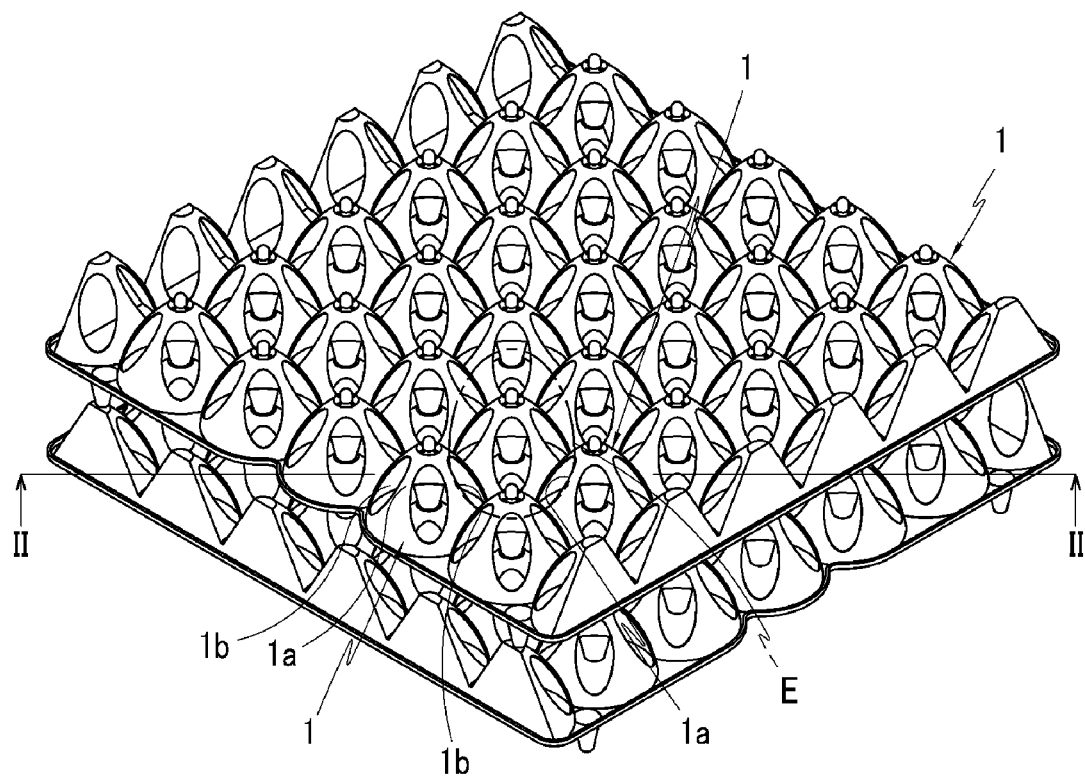
FIG. 1 is a perspective view that illustrates an exemplary embodiment of the present invention.
Figure 2:
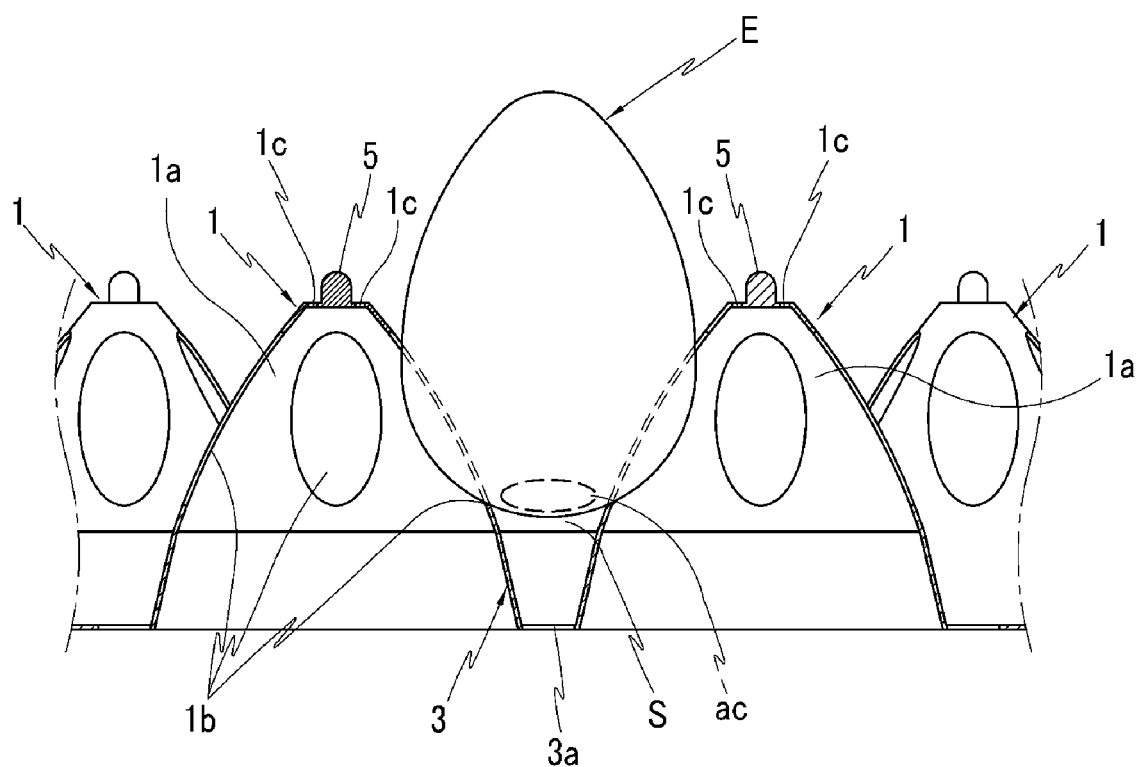
FIG. 2 is a cross-sectional view taken along the line II-II of FIG. 1.
Figure 3:
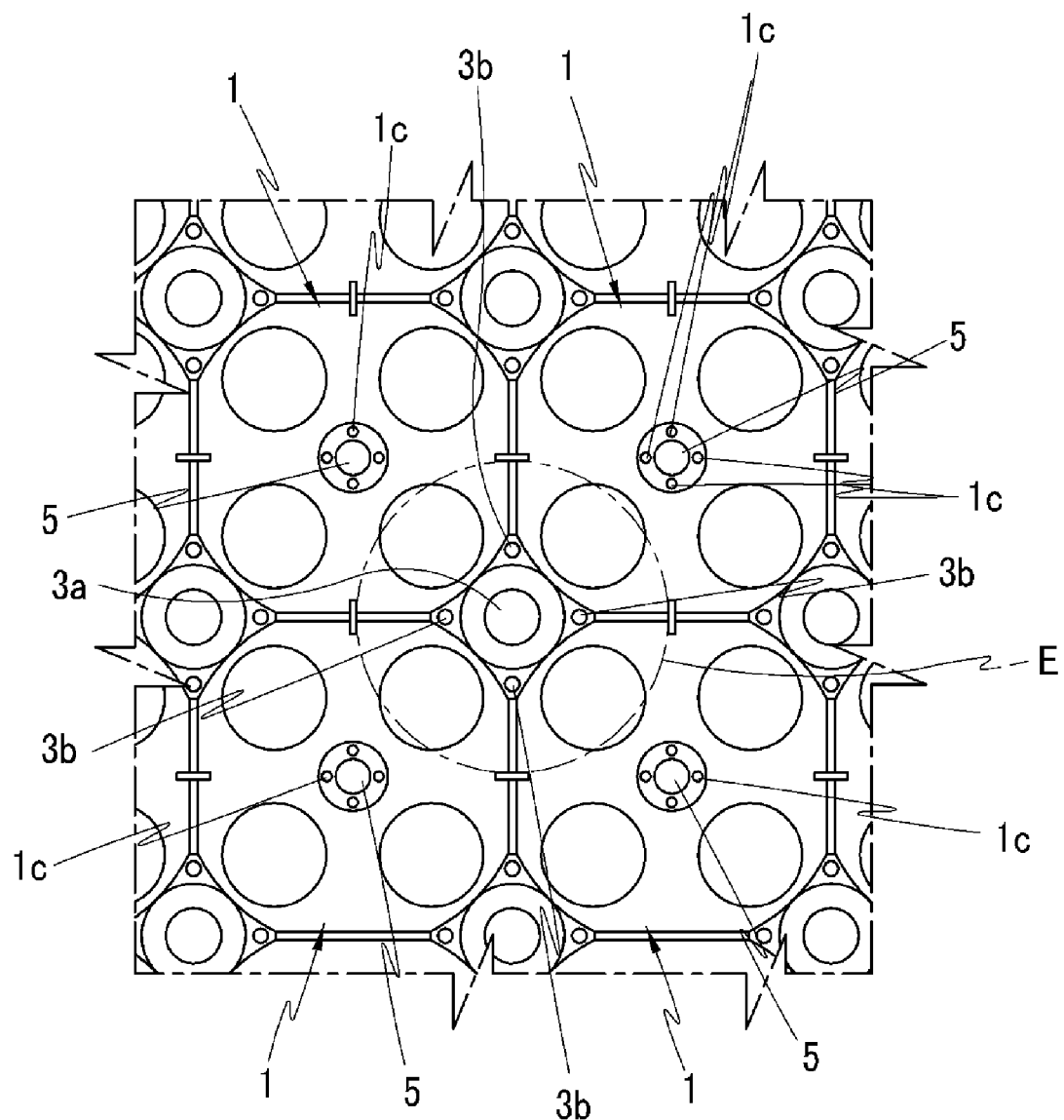
FIG. 3 illustrates a portion of a plan view of FIG. 1.

FIG. 1 is a perspective view that illustrates an exemplary embodiment of the present invention, FIG. 2 is a cross-sectional view that is taken along the line II-II of FIG. 1, and FIG. 3 illustrates a portion of a plan view of FIG. 1 and shows the egg tray. In an exemplary embodiment of the present invention, there is an egg tray in which two layers are layered, but the present invention is not limited thereto, and the egg tray may have two or more layers.

The egg tray according to an exemplary embodiment of the present invention includes convex parts 1 that are disposed at a predetermined interval and connected to each other, bottom parts 3 that are disposed in an opposite direction with respect to the direction of the convex parts 1 at the point where the convex parts 1 are connected to each other, and guide parts 5 that are provided on the upper part of the convex parts 1.

The convex parts 1 that are continuously disposed at a predetermined interval have a convex shape such that inclined sides 1a forming the lateral part of the external circumference are tapered upward. The eggs E are disposed between the convex parts 1, and in order to minimize the contact area between the convex parts 1 and the eggs E, preferably 4 or more egg insertion holes 1b are formed on the inclined sides 1a at a predetermined interval. In other words, the eggs may be disposed between the convex parts 1 while a part thereof is inserted in the egg insertion holes 1b. Accordingly, the contact area between the egg trays and the eggs may be minimized. This configuration allows the eggs to be exposed to the outside while the eggs are not covered by the egg trays in the processing process such as the washing, the heating, and the drying of the eggs, thus maximizing the processing effects of the same. In these convex parts 1, 20, 30, or 60 eggs may be disposed in one egg tray. However, the exemplary embodiment of the present invention is not limited thereto, and various numbers of eggs may be disposed therein.

The bottom parts 3 are disposed between the convex parts 1, and are protruded in an opposite direction with respect to the direction of the convex parts 3. A hole 3a is formed at the center part of the bottom part 3. When the egg trays are sequentially layered, in these holes 3a of the bottom part 3, the guide parts 5 (since the egg trays that are disposed at the upper part and the lower part thereof have the same shape, for convenience of the description, the same reference numeral is provided to describe it) of the egg trays that are disposed at the lower part thereof are inserted. Therefore, even though several egg trays are layered, the layering state can be safely maintained. In addition, referring to FIG. 3, around the bottom part 3, a plurality of fluid discharging holes 3b are formed. It is preferable that the plurality of fluid discharging holes 3b are disposed at a predetermined interval, and the fluid discharging holes are for quickly discharging water or moisture on the bottom of the egg tray to the outside.

Meanwhile, the guide part 5 is provided to the upper part of the convex part 1. In addition, other fluid discharging holes 1c for discharging fluid are provided at the external circumference of the guide part 5. These fluid discharging holes 1c function to rapidly discharge the fluid from the egg tray so the fluid does not remain. That is, these fluid discharging holes 1c function to discharge the fluid to the outside while the fluid that flows down along the bottom part 3 of the egg trays disposed on the upper part thereof does not remain, thereby efficiently carrying out the drying process.

It is preferable that the egg tray that is disclosed in an exemplary embodiment of the present invention is made of a synthetic resin of a transparent material through which light is capable of passing. Since it is made of the transparent material through which light is capable of passing, even though a plurality of eggs are layered on the egg tray, it is possible to easily check for cracks of a shell of the egg, impurities in the egg, rotting of the egg, or inferior eggs by irradiating light, and thus the production of bad products can be prevented.

Figure 5:
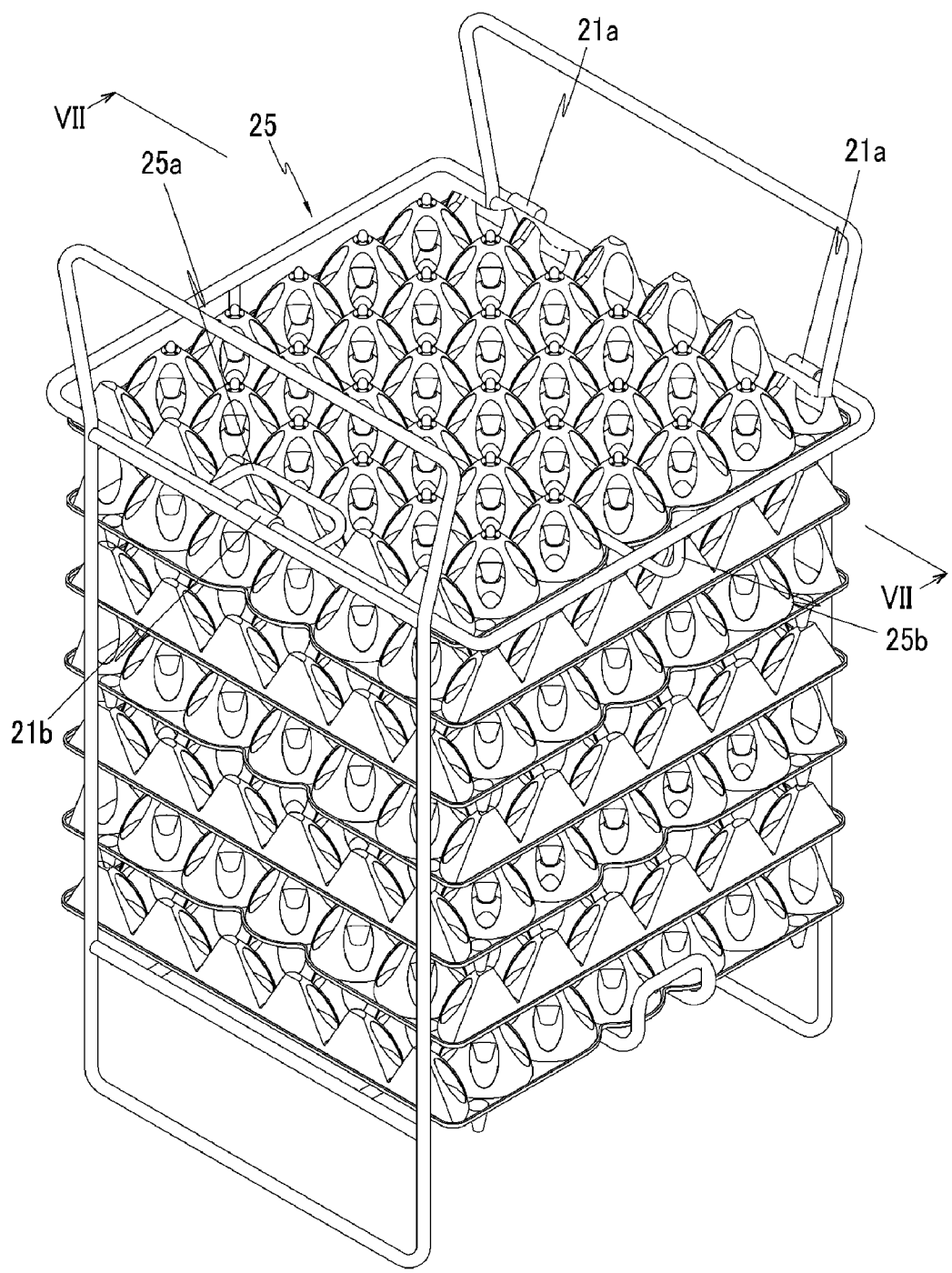
FIG. 5 is a drawing for illustrating an egg tray fixer for layering egg trays and fixing them according to another exemplary embodiment of the present invention.
Figure 6:
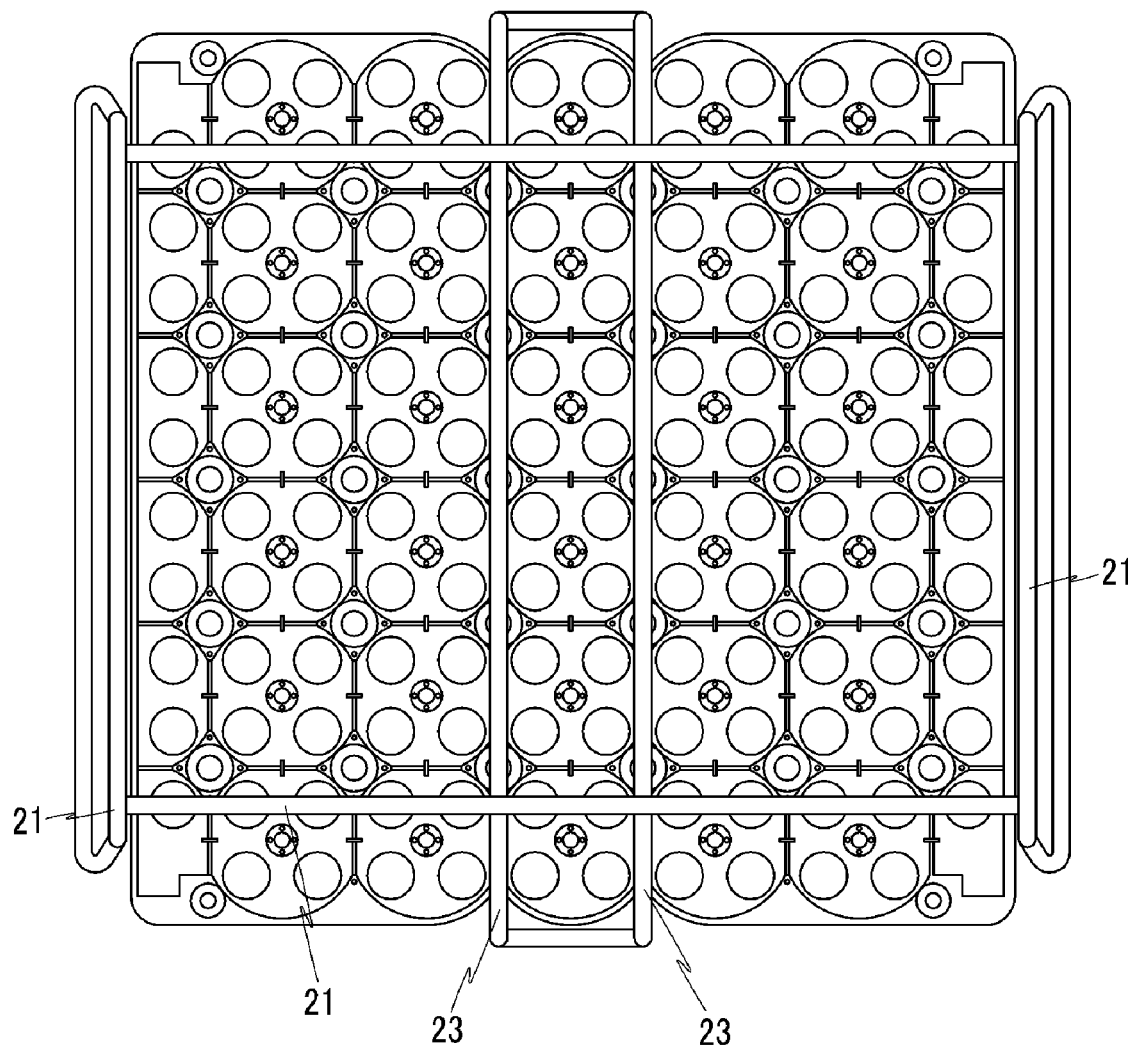
FIG. 6 is a bottom view of FIG. 5.
Figure 7:
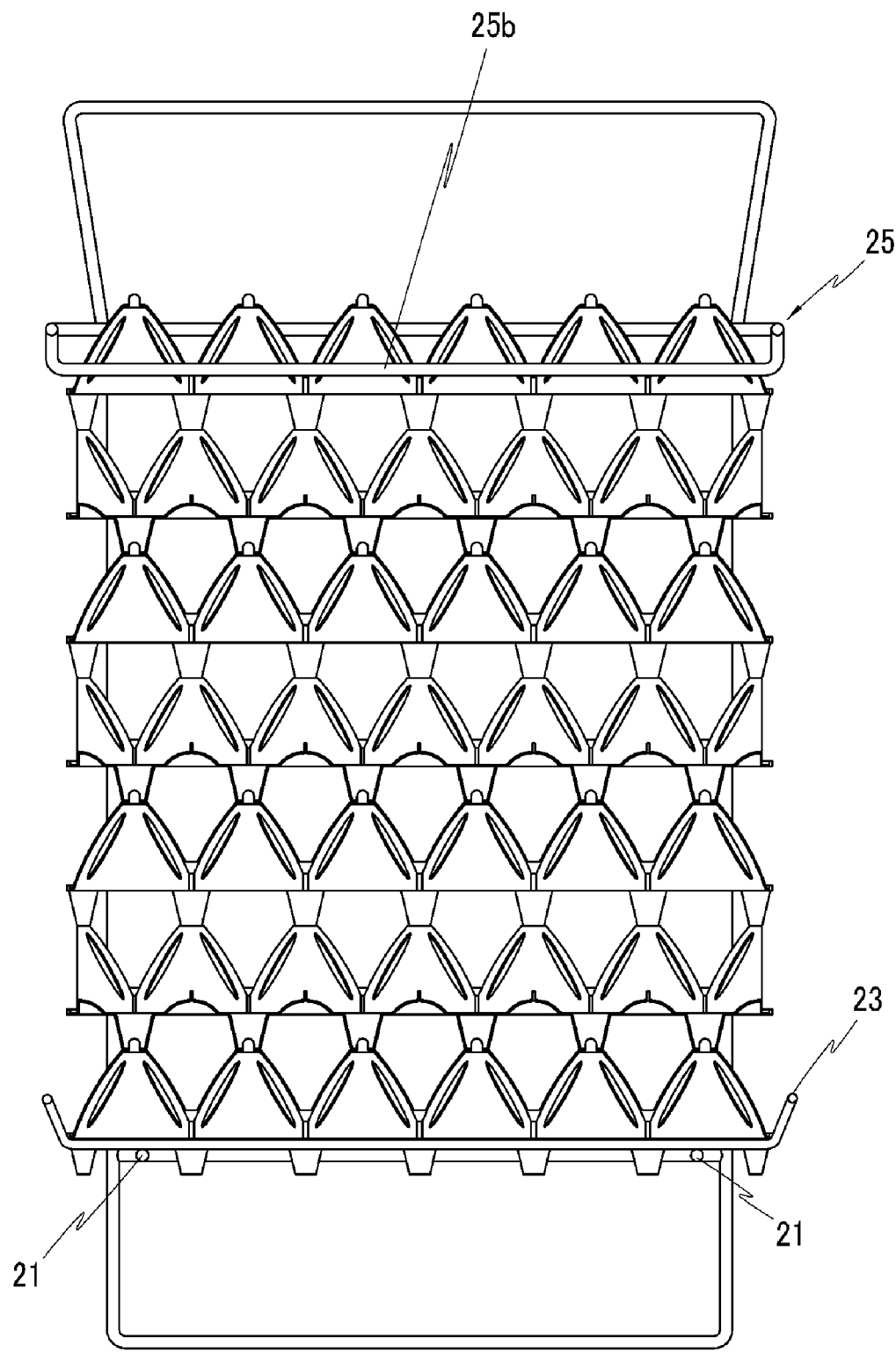
FIG. 7 is a cross-sectional view that is taken along the portion VII-VII of FIG. 5.

An egg tray fixer for fixing the egg trays by layering a plurality of egg trays will now be described with reference to FIGS. 5 to 7. The egg tray fixer is used for coping with movement or the rotation of the entire egg tray, which is caused by the processing of the egg, while the layered egg trays are fixed to each other. This egg tray fixer includes a first member 21 that is closely adhered to the bottom side and the lateral part of the egg tray, and a second member 25 that is hinged to the first member 21 at the upper side of the egg tray to fix the egg trays in conjunction with the first member. The first member 21 is a thin and long metal member such that it can be closely adhered to the bottom side and both lateral parts thereof. The first member 21 supports the bottom side and both lateral parts of the layered egg trays by having the thin and long metal members welded at a predetermined interval. The first members 21 may be welded and disposed in a direction where the thin and long metal members cross each other so that the fixing state of the layered egg trays become more stable. In addition, an auxiliary member 23 that is combined with the first member 21 so that the auxiliary member and the first member cross each other may be disposed on the bottom side of the layered egg trays. The auxiliary member 23 functions to assist in the fixing of the egg trays so that they are capable of being disposed in a row at the same position. In addition, the auxiliary member 23 may be disposed at the bottom side of the egg tray and a part of an end thereof is extended to the lateral part of the egg tray so that the end of the auxiliary member is closely adhered to the lateral part of the egg tray. The structure of the auxiliary member enables the egg trays to be more stably fixed.

In addition, the first member 21 is provided with a plurality of hinge parts 21a that are hinged to the second member 25 at a portion of the upper part thereof, and a fastening part 21b that is capable of fixing the second member 25 at the opposite side thereof. The hinge part 21a hinges to cover the upper part of the egg tray and to fix it. In addition, the fastening part 21b may be fixed while the second member 25 that hinges on the hinge part 21a is closely adhered to the upper part of the egg tray, and has a vertical opening (on the basis of FIG. 5), and thus an end of the second member 25 is fastened thereto. The first member 21 and the second member 25 are not limited to examples that are disclosed in an exemplary embodiment of the present invention, and any structure can be used as long as they have a combination structure where the egg trays are aligned vertically and fixed. The second member 25 may include a separate handle 25a, and may have a structure in which another auxiliary member 25b is combined with the center part thereof.

In an exemplary embodiment of the present invention, the first member 21 and the second member 25 that form the egg tray fixer are not limited to examples that are disclosed in the present invention, but they can have various shapes and constitutions as long as they have a structure in which the layering state is capable of being maintained even when the egg trays move or the entire body is rotated.

When the eggs are put in the egg tray to be processed in a liquid or gas, if the egg tray is moved or rotates from 180° to 360° while the eggs are included in the egg tray by using a robot or a typical moving or rotating device, the egg tray fixer fixes the eggs so that the eggs are not shaken or moved to prevent breakage of the eggs and to maintain the layering state. Due to the upward and downward rotation of the layered egg trays, liquid (water, steam, washing solution, and the like) that is collected in the bottom thereof because of gravity spreads widely and uniformly, and thus the drying rapidly occurs. This configuration allows a large amount of eggs to be quickly dried, and thus time can be reduced and productivity is improved. In addition, since cuticles of the eggshell are easily dissolved in fluid such as water or steam, it is necessary to rapidly remove or dry the fluid (water or steam) to rapidly perform the coating process which is an addition process for rapidly compensating cuticle damage (which is necessarily caused by the egg processing in the fluid) so that a risk of infection of toxic external microorganisms is reduced until the coating process time, thus improving the stability of the egg.

Figure 8:
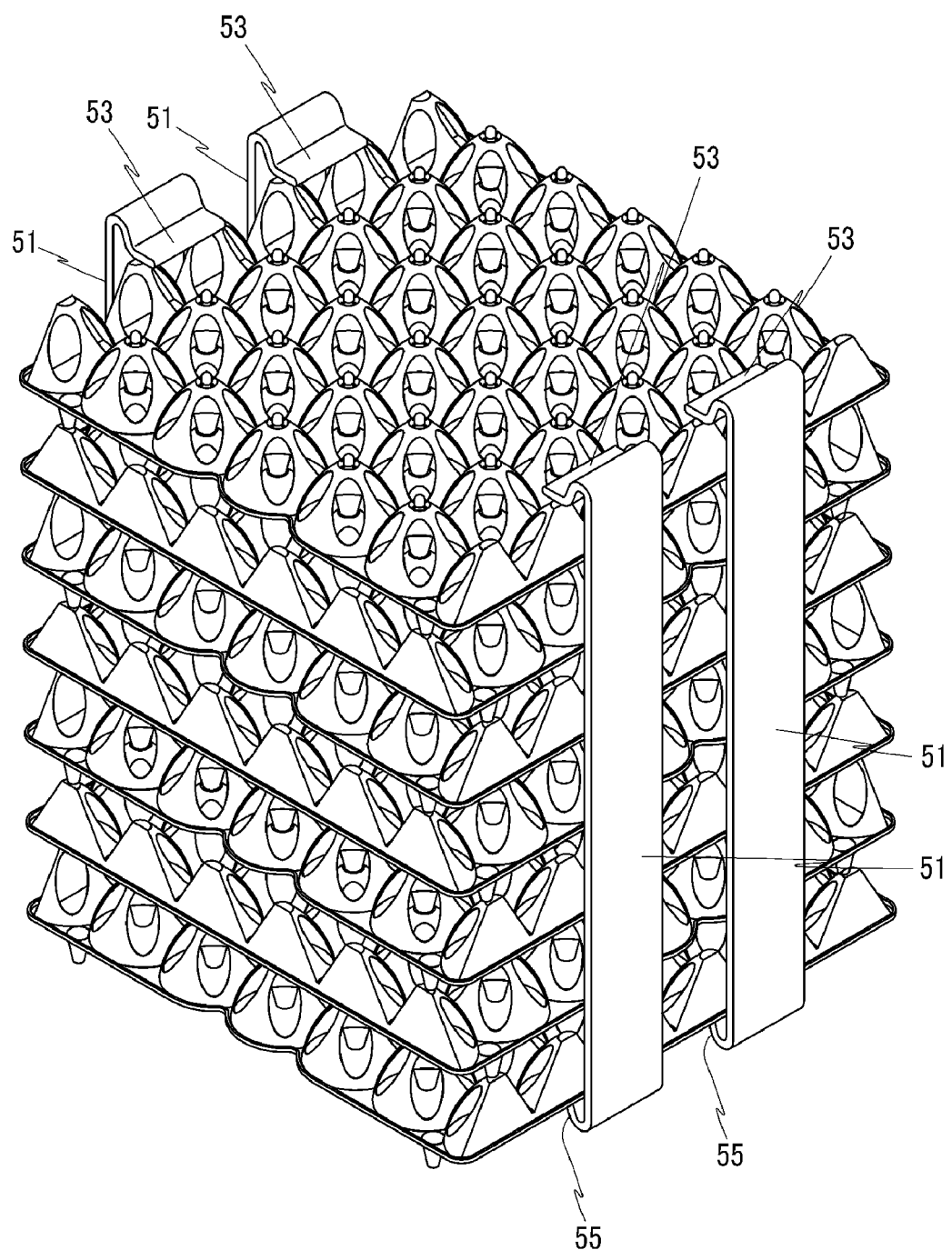
FIG. 8 is a drawing for illustrating another exemplary embodiment of FIG. 5.
Figure 9:
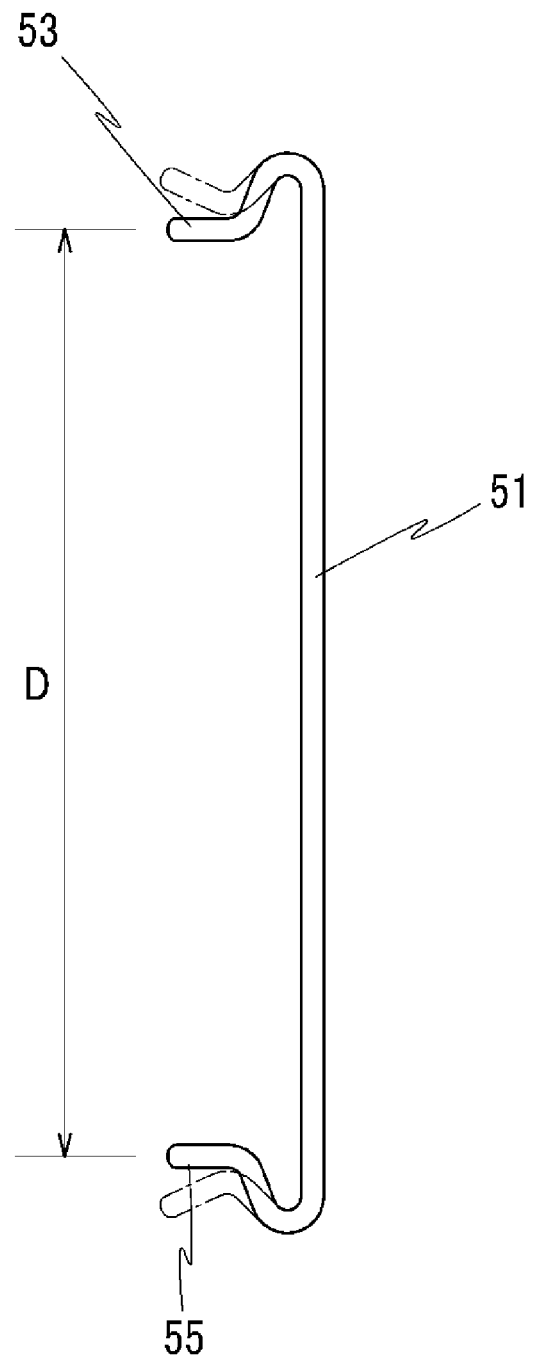
FIG. 9 is a side view that illustrates a main portion of FIG. 8.

FIG. 8 is a drawing for illustrating another exemplary embodiment of the egg tray fixer, and FIG. 9 is a side view that illustrates one of the egg tray fixers. In an exemplary embodiment of the present invention, the egg tray fixer includes a support part 51 that is disposed on the lateral part of the layered egg trays, and elastic parts 53 and 55 that are extended from both ends of the support part 51 and bent toward the egg tray. The elastic parts 53 and 55 receive an elastic force in a direction from the upper part to the lower part of the layered egg trays, thus maintaining the layering state of the egg trays. It is preferable that the support part 51 is relatively thin in the egg tray fixer. In addition, in an exemplary embodiment of the present invention, it is preferable that two or four egg tray fixers are used while they form pairs. FIG. 9 illustrates one of the egg tray fixers as an example thereof. In the elastic parts 53 and 55 of the egg tray fixer, the elastic force is applied in a direction in which a distance D is reduced (direction in which the elastic parts come closer to each other), and the egg tray is fastened between the elastic parts. An exemplary embodiment of the present invention shows the production by simply forming the egg tray fixer.

By an exemplary embodiment of the present invention as described above, a process for sterilizing the egg and boiling the egg soft or hard will be described in detail below.

First, an egg is disposed between convex parts 1 of the egg tray (S1, see FIG. 1). An air chamber of the egg is disposed at the round portion of the egg, and it is more preferable that the egg is disposed between the convex parts 1 of the egg tray so that the air chamber (ac: air cell) faces downward. As described above, since the air chamber of the egg is disposed to face downward, the fluid such as water, steam, the washing solution, and the like that is on the shell of the egg while it is washed or processed in the fluid during the drying process spreads as wide as possible, thus the drying efficiency can be improved (in the case of when the air chamber face upward while the egg is processed, the pointed portion of the egg is disposed at the lower part, and since the liquid is collected at the pointed portion because of gravity, it takes a long time to dry). In addition, the egg is disposed between the convex parts 1 of the egg tray and a portion of the lateral part of the egg is inserted into the egg insertion hole 1b that is provided at the convex part 1. The disposing structure of the egg minimizes the contact area between the egg tray and the egg to rapidly carry out the heating or drying process in the egg processing such as the sterilization, the washing, the boiling soft or hard, and the like. In addition, the egg is disposed while the bottom end spaces S (shown in FIG. 2) are maintained. As described above, the eggs are disposed in the egg tray and a plurality of egg trays in which the eggs are disposed are layered (S3). In general, the layering of the egg tray may be carried out within a range of from 2 layers to 18 layers, and the number of layered egg trays is not limited but may vary if necessary. In addition, the layered egg trays are fixed by using the egg tray fixer (S5). The method for fixing the layered egg trays by using the egg tray fixer is to dispose the first member 21 on the bottom side and both lateral parts of the egg tray and to fasten an end of the second member 25 to the fasten part 21b of the first member 21 at the upper surface thereof as described in the description of the configuration of the egg tray fixer (see FIG. 6). In addition, the eggs that are disposed in the egg trays that are layered are washed (S7). At this time, the eggs are washed in a gas (including steam) or liquid, or by spraying the gas or the liquid. The washed eggs are heated in order to be sterilized and boiled soft or hard (S9). It is preferable that when the eggs are heated, the temperature of the heating source becomes higher than the temperature of the egg by 11° C. or more. As described above, a temperature difference between the eggs and the heating source is maintained in order to prevent the permeation of external toxic microorganisms into the eggs because an inverse osmotic pressure occurs. By the structure of the egg tray that is disclosed in an exemplary embodiment of the present invention, a structure in which the contact area between the eggs and the egg tray is minimized is disposed, and thus the heat transferring can be relatively uniformly carried out, thereby further reducing the heating process time.

Continuously, the eggs are sterilized and boiled soft or hard by heating them (S11). In addition, through the operation such as the heating of the gas, the sterilized eggs are dried (S13). In an exemplary embodiment of the present invention, in the drying process, the gas or liquid is rapidly discharged through the hole 3a of the bottom part 3, and a plurality of fluid discharging holes 3b and 1c, and the contact area between the eggs and the egg tray is minimized to maximize the drying efficiency. In addition, in the drying process, the layered egg trays may be dried while being rotated 180° or 360°, and the upper and lower directions are changed by using a typical rotation device in order to obtain the rapid drying. In this process, without the problems in which the fluid such as water or steam that is on the specific portion of the surface (shell) of the egg is collected at one portion at the bottom of the egg because of gravity and it takes a long time to dry it, the liquid is uniformly spread and the drying is rapidly carried out. In the drying process, the reduction of the drying time reduces the infection of the toxic microorganisms from the outside, increases the productivity, and the increase of the drying efficiency reduces the waiting time until the coating process which is the post process and increases the efficiency of the coating process to improve the stability against infection of the toxic microorganisms.

After the drying, it is coated (S15). After the eggs having the shells are put in the egg tray and subjected to the post process such as the washing and heating in the gas (including steam) or liquid, since the cuticle of the eggshell is dissolved in the gas or the liquid that is used in the processing or is damaged, there is a very high risk of the egg being infected by the external toxic microorganisms, thus it is preferable that the coating process is carried out before packing. For this purpose, the egg is coated with an edible mineral oil and the like to reduce the damaged cuticles. Through the coating process, the safety of the egg can be more improved.

Figure 4:
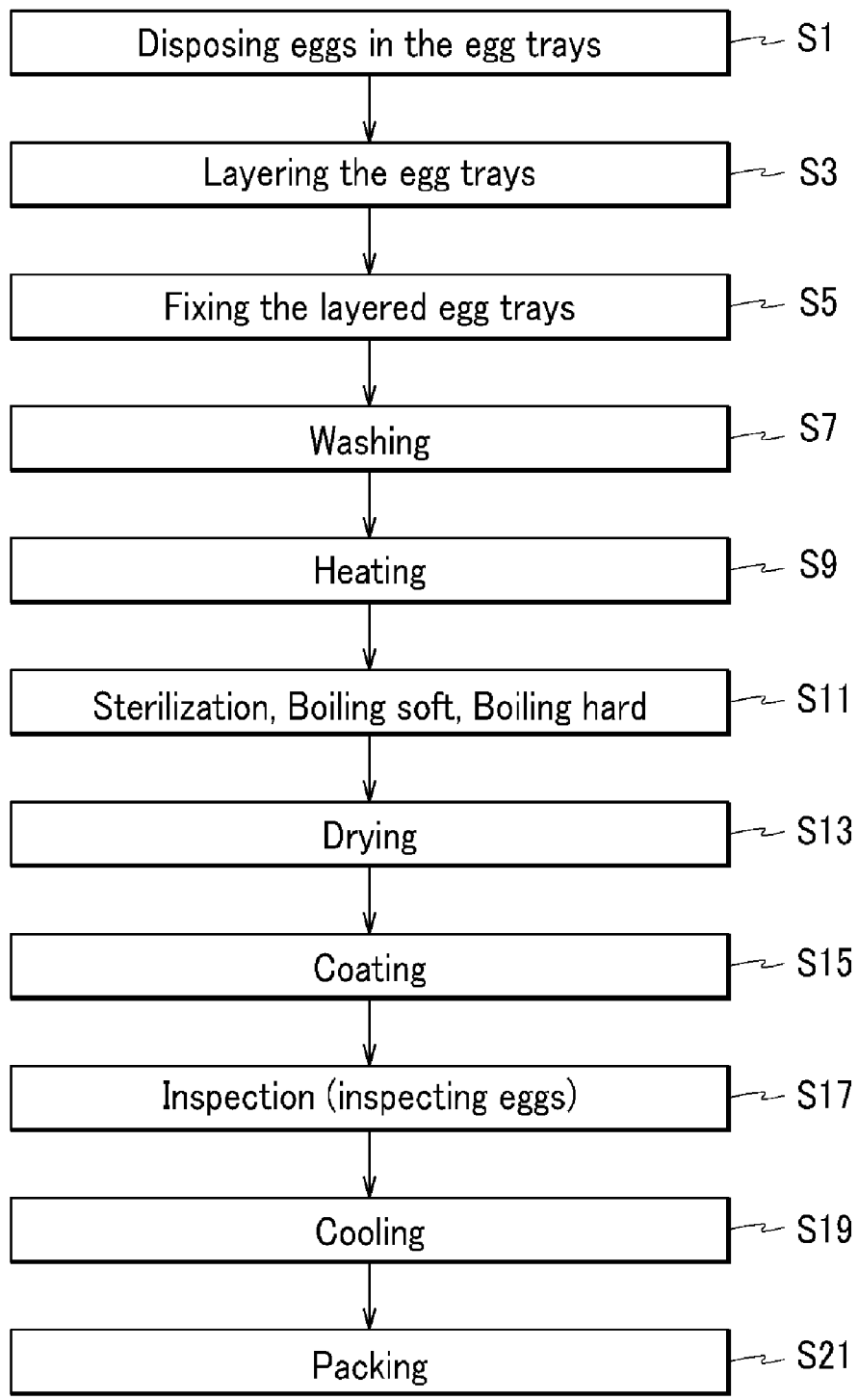
FIG. 4 is a flowchart for illustrating a process for processing an egg according to an exemplary embodiment of the present invention.

After the coating process, the egg is inspected (S17) and cooled (S19). The inspection process is carried out after the coating process is carried out in FIG. 4, but is not limited thereto, and it can be frequently carried out in the whole process. Particularly, in an exemplary embodiment of the present invention, when the egg tray is made of a transparent synthetic resin material having the light transmission property, by irradiating light to transmit light, the inside and the outside of the eggs that are disposed in a large amount can be easily inspected. In the description of the present exemplary embodiment, the inspection process (S17) of the egg is to inspect damage to the egg that is capable of being caused by the heating of the eggs. Next, it is packed (S21).

As described above, the present invention has the effect in which the drying is rapidly carried out to prevent moisture from remaining on the egg before the packing treatment when the egg is subjected to the processing such as the washing, the sterilizing, the boiling soft or hard, and the like in liquid or gas (including steam) and the coating process is shortened to reduce the operation time while the eggs are subjected to the processing such as the washing, the sterilizing, the boiling soft or hard, and the like and to process the eggs in a large amount, thus improving the productivity. In addition, by reducing the infection of the microorganism caused by damage of cuticles that prevents infection of the microorganism, the stability and the value of the commodity that are required for foods are increased.

In addition, the present invention has the effect in which, by using the light transmissive egg tray to easily check for bad eggs, cracks of the shell or the circulation of the bad eggs can be prevented to more increase the safety of the foods.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A process for treating eggs in an egg tray that comprises a plurality of convex parts that are disposed at a predetermined interval and a plurality of bottom parts that are protruded in an opposite direction with respect to the convex parts and in which inclined sides that form lateral parts of the convex parts are convex and egg insertion holes are formed in the inclined sides by using the egg tray, the process comprising:

disposing the eggs between the convex parts of the egg tray so that a rounded end of the eggs in the egg tray faces downward, and such that the eggs are positioned in the egg insertion holes;

layering a plurality of the egg trays;

washing the eggs that are received in the layered egg trays;

heating the eggs after washing the eggs;

sterilizing the eggs after heating the eggs;

boiling the eggs soft or hard after sterilizing the eggs;

drying the eggs after boiling the eggs; and coating the eggs by using a protective oil.

2. The process for treating eggs by using an egg tray of claim 1, further comprising, after coating the eggs, cooling the eggs.

3. The process for treating eggs by using an egg tray of claim 1, further comprising, after washing the eggs, irradiating light to the eggs to inspect the presence of defects of the eggs.

4. The process for treating eggs by using an egg tray of claim 1, further comprising, after layering the egg trays, fixing the egg trays by using a fixing member so that the layered egg trays are fixed to each other.

5. A process for treating eggs, the process comprising:

providing a first egg tray and a second egg tray, wherein each of the first and second egg trays has (a) a plurality of convex parts having an egg insertion hole formed therein, and (b) a bottom connection part that connects adjacent convex parts and that has a bottom fluid discharge hole formed therein;

disposing a first plurality of eggs into the first egg tray such that each of the first plurality of eggs sits within an egg insertion hole and has its rounded end positioned above, but spaced apart from, the bottom fluid discharge hole;

disposing a second plurality of eggs into the second egg tray such that each of the second plurality of eggs sits within an egg insertion hole and has its rounded end positioned above, but spaced apart from, the bottom fluid discharge hole;

stacking the second egg tray above the first egg tray;

washing the first and second pluralities of eggs in the stacked first and second egg trays;

after washing, heating the first and second pluralities of eggs in the stacked first and second egg trays;

after washing, sterilizing the first and second pluralities of eggs in the stacked first and second egg trays;

after washing, cooking the first and second pluralities of eggs in the stacked first and second egg trays;

after cooking, drying the first and second pluralities of eggs in the stacked first and second egg trays; and applying a protective oil to the first and second pluralities of eggs in the stacked first and second egg trays.

6. The process of claim 5, wherein each of the first and second pluralities of eggs sits within four egg insertion holes.

7. The process of claim 5, wherein:

the first egg tray also includes a top connection part that (a) connects adjacent convex parts, (b) has an upwardly-protruding guide part and (c) includes a top fluid discharge hole formed therein;

the second egg tray also includes a guide hole formed in the bottom connection part; and stacking the second egg tray above the first egg tray further comprises (a) inserting the upwardly-protruding guide part of the first egg tray into the guide hole of the second egg tray and (b) aligning the top fluid discharge hole of the first egg tray with the bottom fluid discharge hole of the second egg tray.

8. The process of claim 5, further comprising:
attaching an egg tray fixer to the first egg tray after stacking the first and second egg trays but before washing the first and second pluralities of eggs;
wherein the egg tray fixer includes a first member that is at least partially positioned below the first egg tray, and
wherein the egg tray fixer further includes a second member that is at least partially positioned above the second egg tray, and that is attached to the first member via a hinge.

9. The process of claim 5, further comprising:
attaching a plurality of egg tray fixers to the first egg tray after stacking the first and second egg trays but before washing the first and second pluralities of eggs;
wherein each of the tray fixers include (a) a lower elastic part configured to be clamped onto the first egg tray and (b) an upper elastic part configured to be claimed onto an egg tray that is stacked above the first egg tray.

* * * * *